(12) United States Patent
Ranucci

(10) Patent No.: US 7,931,601 B2
(45) Date of Patent: Apr. 26, 2011

(54) MONITORING SYSTEM FOR CARDIAC SURGICAL OPERATIONS WITH CARDIOPULMONARY BYPASS

(75) Inventor: Marco Ranucci, Milan (IT)

(73) Assignee: Sorin Group Italia S.r.l., Mirandola (MO) (IT)

(*) Notice: Subject to any disclaimer, the term of this patent is extended or adjusted under 35 U.S.C. 154(b) by 248 days.

(21) Appl. No.: 12/250,221

(22) Filed: Oct. 13, 2008

(65) Prior Publication Data

US 2009/0043219 A1  Feb. 12, 2009

Related U.S. Application Data

(62) Division of application No. 11/432,608, filed on May 11, 2006, now Pat. No. 7,435,220.

(30) Foreign Application Priority Data

May 13, 2005 (IT) .................... MI20050866
Oct. 4, 2005 (EP) ...................... 05021607

(51) Int. Cl.
*A61B 5/08* (2006.01)
*F16K 31/02* (2006.01)

(52) U.S. Cl. .................... 600/532; 600/538; 128/204.23
(58) Field of Classification Search .......... 600/523–543, 600/484; 128/204.21, 204.22, 204.23, 204.26
See application file for complete search history.

(56) References Cited

U.S. PATENT DOCUMENTS

| 5,251,632 A | 10/1993 | Delpy |
| 5,365,922 A | 11/1994 | Raemer |
| 5,402,796 A * | 4/1995 | Packer et al. ................. 600/532 |
| 5,551,435 A | 9/1996 | Sramek |
| 5,591,399 A * | 1/1997 | Goldman et al. ............... 422/44 |

(Continued)

FOREIGN PATENT DOCUMENTS

EP  1 514 562 A2  3/2005

(Continued)

OTHER PUBLICATIONS

Joachimsson et al., "Adverse Effects of Hyperoxemia During Cardiopulmonary Bypass", Journal of Thoracic and Cardiovascular Surgery, Mosby-Year Book, Inc., St. Louis, MO, U.S., 112(3):812-819 (Sep. 1996).

(Continued)

*Primary Examiner* — Charles A Marmor, II
*Assistant Examiner* — Navin Natnithithadha
(74) *Attorney, Agent, or Firm* — Faegre & Benson, LLP

(57) ABSTRACT

A monitoring system for cardiac operations with cardiopulmonary bypass comprising: a processor operatively connected to a heart-lung machine; a pump flow detecting device connected to a pump of the heart-lung machine to continuously measure the pump flow value and send it to the processor; a hematocrit reading device inserted inside the arterial or venous line of the heart-lung machine to continuously measure the blood hematocrit value and to send it to the processor; a data input device to allow the operator to manually input data regarding the arterial oxygen saturation and the arterial oxygen tension; computing means integrated in the processor to compute the oxygen delivery value on the basis of the measured pump flow, the measured hematocrit value, the preset value of arterial oxygen saturation, and the preset value of arterial oxygen tension; and a display connected to the processor to display in real-time the computed oxygen delivery value.

5 Claims, 6 Drawing Sheets

U.S. PATENT DOCUMENTS

| | | | |
|---|---|---|---|
| 5,634,461 | A | 6/1997 | Faithfull et al. |
| 5,682,877 | A | 11/1997 | Mondry |
| 5,743,268 | A | 4/1998 | Kabal |
| 5,752,509 | A * | 5/1998 | Lachmann et al. ...... 128/204.23 |
| 5,788,647 | A | 8/1998 | Eggers |
| 5,931,779 | A | 8/1999 | Arakaki et al. |
| 5,937,858 | A * | 8/1999 | Connell .................. 128/207.14 |
| 5,978,691 | A | 11/1999 | Mills |
| 6,098,617 | A * | 8/2000 | Connell .................. 128/200.26 |
| 6,144,444 | A | 11/2000 | Haworth et al. |
| 6,234,963 | B1 | 5/2001 | Blike et al. |
| 6,390,977 | B1 | 5/2002 | Faithfull et al. |
| 6,512,938 | B2 | 1/2003 | Claure et al. |
| 6,581,595 | B1 * | 6/2003 | Murdock et al. ......... 128/204.18 |
| 6,671,529 | B2 | 12/2003 | Claure et al. |
| 6,675,798 | B1 | 1/2004 | Tyomkin et al. |
| 6,706,007 | B2 | 3/2004 | Gelfand et al. |
| 6,743,172 | B1 | 6/2004 | Blike |
| 7,435,220 | B2 * | 10/2008 | Ranucci ....................... 600/483 |
| 2004/0217054 | A1 | 11/2004 | Olsen et al. |
| 2006/0257283 | A1 * | 11/2006 | Ranucci ......................... 422/45 |
| 2009/0043173 | A1 | 2/2009 | Ranucci |
| 2009/0043212 | A1 | 2/2009 | Ranucci |
| 2009/0043219 | A1 * | 2/2009 | Ranucci ....................... 600/532 |

FOREIGN PATENT DOCUMENTS

| | | |
|---|---|---|
| JP | 2001-505808 A | 5/2001 |
| JP | 2002-200164 A | 7/2002 |
| JP | 2002-542900 A | 12/2002 |
| WO | WO 98/25514 A1 | 6/1998 |
| WO | WO 00/66197 A1 | 11/2000 |

OTHER PUBLICATIONS

May 14, 2007 International Search Report in European counterpart Application No. EP 05 02 1607 (5 pages).

Demers et al., "Outcome with high blood lactate levels during cardiopulmonary bypass in adult cardiac surgery", Ann Thorac Surg, 70: 2082-6 (2000).

Fang et al., "Impact of minimum hematocrit during cardiopulmonary bypass on mortality in patients undergoing coronary artery surgery", Circulation, 96(suppl II):194-9 (1997).

Habib et al. "Adverse effects of low hematocrit during cardiopulmonary bypass in the adult: should current practice be changed?", J Thorac Cardiovasc Surg, 125: 1438-50 (2003).

Karkouti et al., "Hemodilution during cardiopulmonary bypass is an independent risk factor for acute renal failure in adult cardiac surgery", J Thorac Cardiovasc Surg, 129: 391-400 (2005).

Ranucci et al., "Acute renal injury and lowest hematocrit during cardiopulmonary bypass: not only a matter of cellular hypoxemia", Ann Thorac Surg, 78:1880-1 (2004).

Ranucci et al., "Oxygen delivery during cardiopulmonary bypass and acute renal failure following coronary operations", Ann Thorac Surg, 80(6):2213-2220 (Dec. 2005).

Ranucci et al., "Risk factors for renal dysfunction after coronary surgery: the role of cardiopulmonary bypass technique", Perfusion, 9:319-26 (1994).

Stafford-Smith et al., "Low hematocrit but not perfusion pressure during CPB is predictive for renal failure following CABG 30 surgery" [Abstract], Anesth Analg, 86:SCA1-SCA124 (1998).

Swaminathan et al. "The association of lowest hematocrit during cardiopulmonary bypass s with acute renal injury after coronary artery bypass surgery", Ann Thorac Surg, 76: 784-92 (2003).

U.S. Appl. No. 12/250,201, filed Oct. 13, 2008 (27 pages).

U.S. Appl. No. 12/250,212, filed Oct. 13, 2008 (29 pages).

Abstract for JP 2002-200164 A (1 page).

Computer translation of JP 2002-200164 A (14 pages).

* cited by examiner

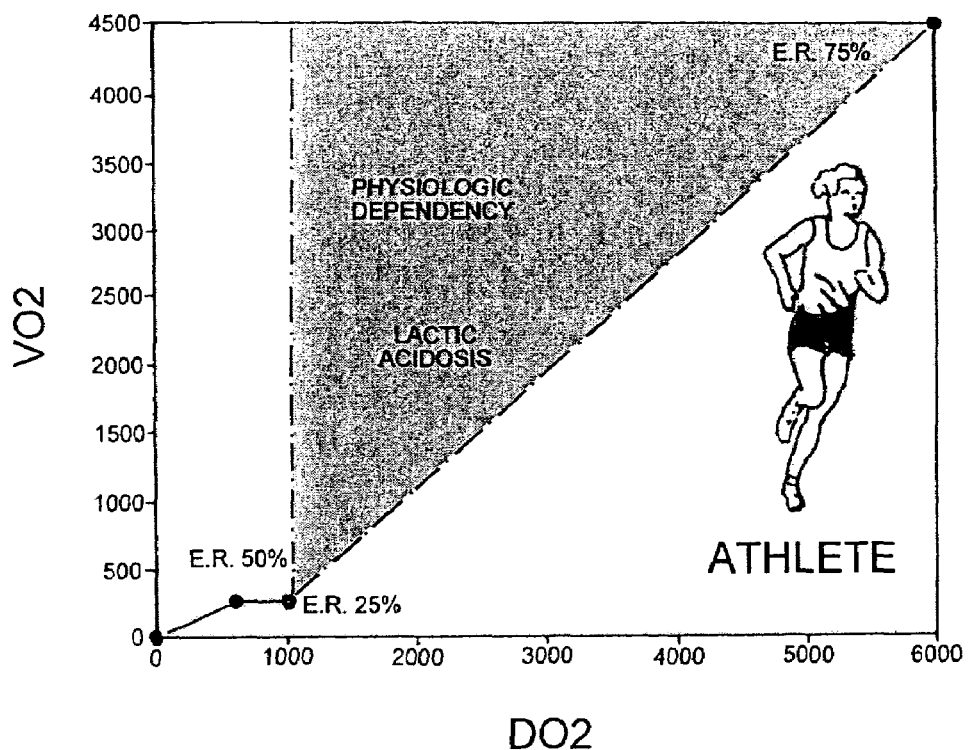
FIG. 1
FIG. 2
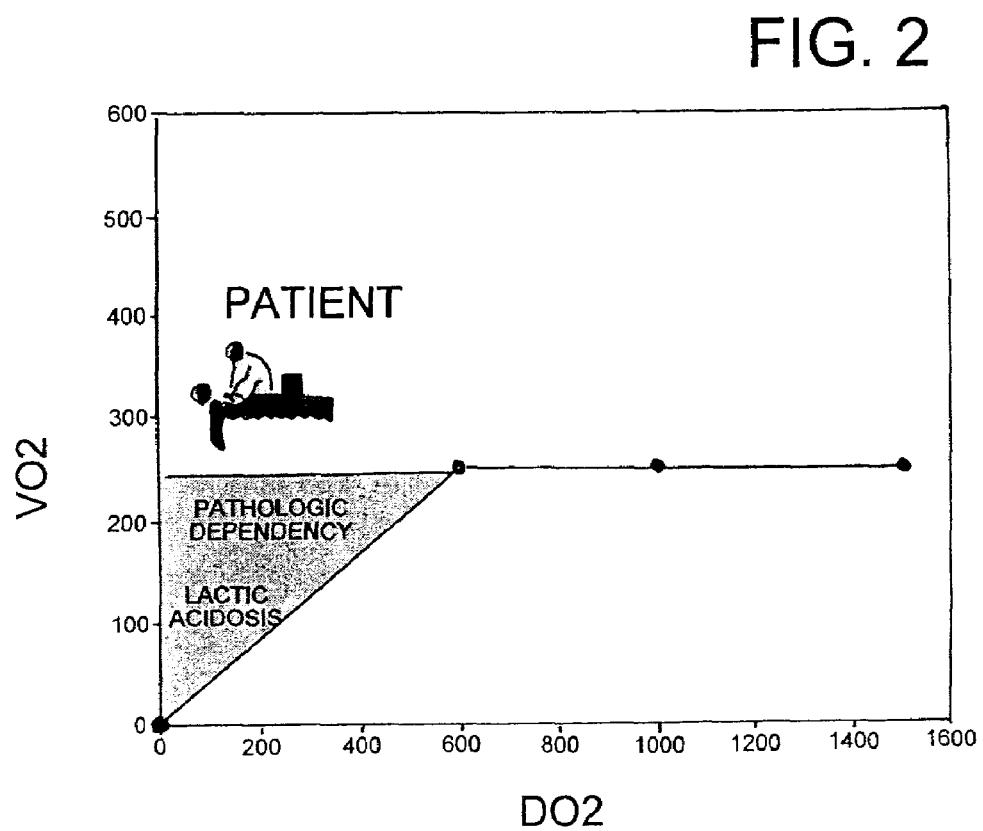

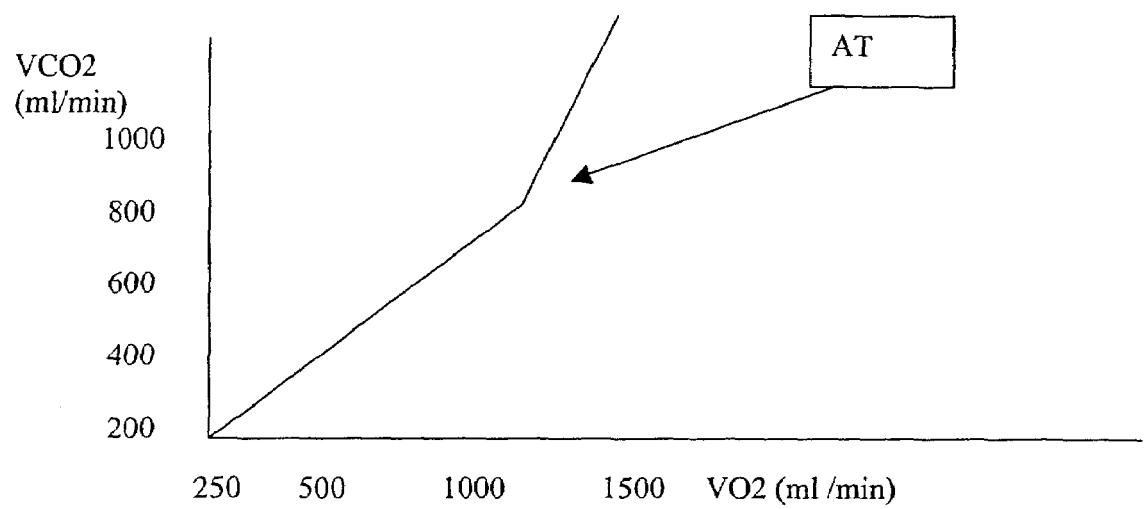
FIG. 3
FIG. 4
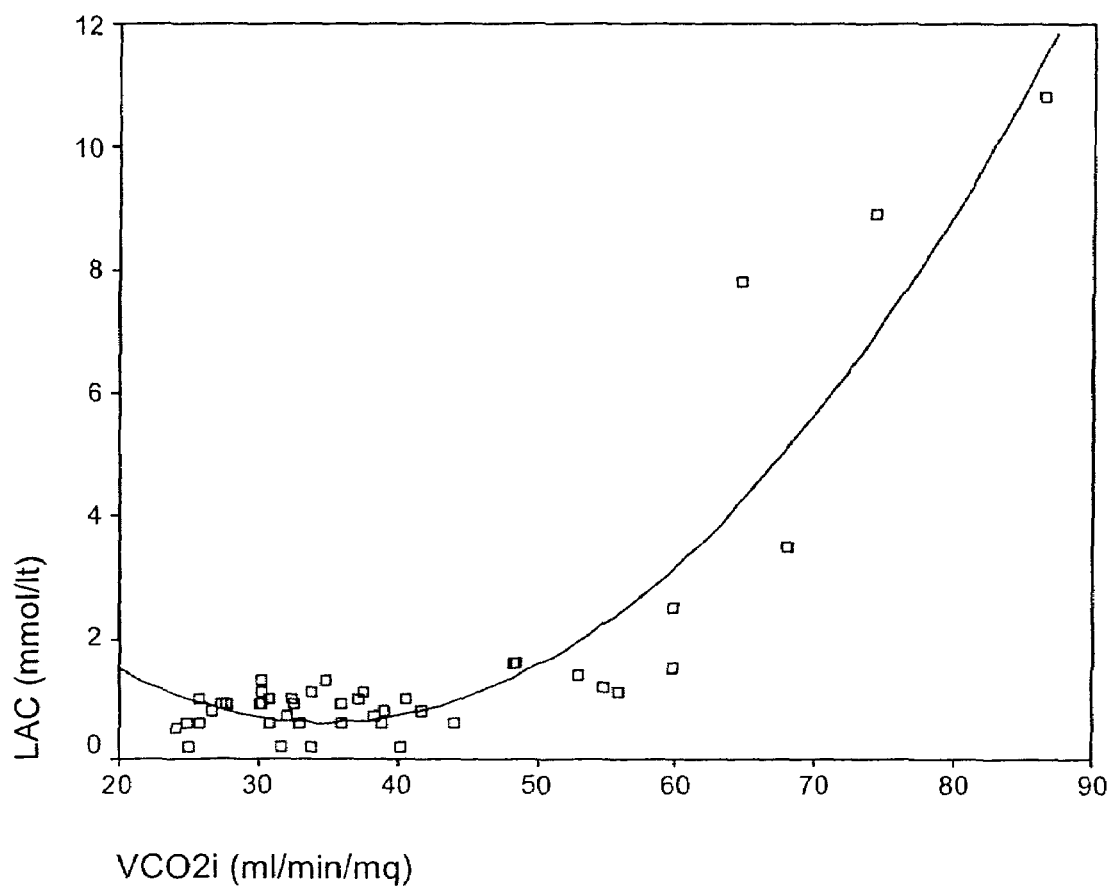

MONITORING SYSTEM FOR CARDIAC SURGICAL OPERATIONS WITH CARDIOPULMONARY BYPASS

This application is a divisional of application Ser. No. 11/432,608, filed May 11, 2006, which claims foreign priority of Italian Patent Application No. MI2005000866, filed May 13, 2005, and European Patent Application No. 05021607.6, filed Oct. 4, 2005, the contents of each of which are hereby incorporated herein by reference.

The present invention provides a monitoring system to be applied during cardiac surgery operations requiring a cardiopulmonary bypass (CPB).

During cardiac operations with extracorporeal circulation and CPB, the heart and lung function is artificially replaced by a heart-lung machine. This device receives the venous blood of the patient and delivers it (through a roller or centrifugal pump) to an oxygenator which provides the carbon dioxide (CO2) clearance and the oxygen (O2) supply to the patient, by means of a trans-membrane exchange between blood and a gas flow (oxygen and air at variable concentrations).

The adequate pump flow for the patient is usually determined on the basis of specific tables which take into account the body surface area and the temperature at which the CPB is performed. The lower the temperature, the lower is the needed pump flow (because the metabolic needs are decreased). For instance, in a temperature range between 24 and 37° C., the flow may vary between 2.0 and 3.0 L/min/m². The goal of the pump flow is to provide to the various organs an oxygen amount adequate to sustain the metabolic needs. This does not depend only on the pump flow, but also on the blood oxygen content and therefore on the hemoglobin (Hb) concentration. Since during CPB there is a hemodilutional anemic status (sometimes severe, with an Hb concentration that falls from the normal 15 g/100 ml to 5-10 g/100 ml), it is clear that the possibility of providing an insufficient oxygen delivery (DO2) is real and quite frequent.

Recently, many scientific papers have demonstrated that insufficient oxygen delivery, either due to excessive anemia, to a low flow, or both, is responsible for postoperative complications and surgical mortality increase (References 1-8).

At present, the only continuous monitoring available of a DO2-derived parameter during CPB is represented by the continuous venous oxygen saturation (SvO2) monitoring. This monitoring is based on the relationship between the oxygen consumption (VO2), that is a metabolic needs marker, the blood flow and the peripheral oxygen extraction (arterovenous difference):

$$VO2 = Flow \times (a\text{-}v\ O2\ difference)$$

If the pump flow is inadequate to maintain the needed VO2, it is necessary to extract more oxygen from the periphery, and hence the venous blood will be less saturated (from the normal 75% the saturation may decrease to 60% or less).

Presently, three venous oxygen saturation (SvO2) systems are commercially available: (DataMaster Dideco™; CDI Terumo™; O2Sat Spectrum Medical™). With the exception of the last one, all these systems measure other variables (hematocrit, electrolytes, etc.) by means of very expensive disposable cells. Therefore, these monitoring systems are not routinely used, and their application is usually reserved for specific, high-risk categories of patients (i.e., congenital, pediatric cardiac surgery patients).

Moreover, the SvO2 measurement is not a guarantee of adequate pump flow. As a matter of fact, the SvO2 decreases only for a very profound DO2 decrease. This is due to the fact that the SvO2 represents the status of the whole venous blood coming from the patient. This blood comes even, and to a great extent, from various organs and districts which, under anesthesia, have a VO2 close to zero (muscles, skin, subcutaneous tissues, etc.) and that therefore contribute to the total venous blood with their own venous blood having a SvO2 close to 100%. Therefore, in case of a low perfusion to one or more among the most important organs (kidney, brain, gut and the heart itself), which determines a venous blood desaturation down to 60%, the total mixing may result in a global SvO2 still in a normal range (70-75%).

The aim of the present invention is to overcome the drawbacks of the prior art and create a monitoring system that provides adequate continuous and on-line information about the oxygen delivery (DO2) and carbon dioxide production (VCO2) values during the operation, and about the adequacy of the oxygen delivery (DO2) with respect to the metabolic needs of the patient.

Another aim of the present invention is to provide a monitoring system which is reliable, accurate, and at the same time cheap and easy to be applied.

These aims are achieved according to the invention by means of the device and method whose characteristics are respectively listed in the attached independent claims. Advantageous embodiments of the invention are apparent from the dependent claims.

The pathophysiological bases used for structuring the monitoring system according to the invention are the following:

DEFINITIONS AND ABBREVIATIONS

HCT: hematocrit (%)
Hb: hemoglobin (g/dL)
CPB: cardiopulmonary bypass
T: temperature (° C.)
VO2=oxygen consumption (mL/min)
VO2i=oxygen consumption indexed (mL/min/m²)
DO2=oxygen delivery (mL/min)
DO2i=oxygen delivery indexed (mL/min/m²)
O2 ER=oxygen extraction rate (%)
VCO2=carbon dioxide production (mL/min)
VCO2i=carbon dioxide production indexed (mL/min/m²)
Ve=ventilation (L/min)
eCO2=exhaled carbon dioxide (mmHg)
AT=anaerobic threshold
LAC=lactates
Qc=cardiac output (mL/min)
IC=cardiac index (Qc/m²), (mL/min/m²)
Qp=pump flow (mL/min)
IP=pump flow indexed (Qp/m²), (mL/min/m²)
CaO2=arterial oxygen content (mL/dL)
Cv O2=venous oxygen content (mL/dL)
PaO2=arterial oxygen tension (mmHg)
PvO2=venous oxygen tension (mmHg)
a=arterial
v=venous
Sat=Hb saturation (%)

The following equations are applied to implement the monitoring system according to the invention:

$$VO2 = Qc \times (CaO2 - CvO2) \text{ in a normal circulation} \quad (1)$$

$$VO2 = Qp \times (CaO2 - CvO2) \text{ during CPB} \quad (2)$$

$$DO2 = Qc \times CaO2 \text{ in a normal circulation} \quad (3)$$

$$DO2 = Qp \times CaO2 \text{ during CPB} \quad (4)$$

$$O2\ ER = VO2/DO2 (\%) \quad (5)$$

$$Hb = HCT/3 \quad (6)$$

$$CaO2 = Hb \times 1.36 \times Sat(a) + PaO2 \times 0.003 \quad (7)$$

$$CvO2 = Hb \times 1.36 \times Sat(v) + PvO2 \times 0.003 \quad (8)$$

$$VCO2 = VexeCO2 \times 1.15 \quad (9)$$

For instance, a normal subject weighing 70 kg has the following physiologic parameters:
Hb=15 g/dL
PaO2=90 mmHg
Sat(a) Hb=99%=0.99
Pv O2=40 mmHg
Sat(v) Hb=75%=0.75
Qc=5000 mL/min
CaO2=15×1.36×0.99+90×0.003=20.4 mL/dL
CvO2=15×1.36×0.75+40×0.003=15.4 mL/dL
VO2=5 L/min× (20.4 mL/dL–15.4 mL/dL)=5 L/min×5 mL/dL=5 L/min×50 mL/L=250 mL/min
DO2=5 L/min×20.4 mL/dL=5 L/min×200 mL/L=1000 mL/min
O2ER=250/1000=25%
VCO2=200 mL/min
LAC=<1.5 mMol/L The oxygen consumption (VO2) represents the metabolic needs of the whole organism; it is the sum of the metabolic needs of each specific organ. Under basal conditions (at rest), it is about 3-4 mL/min/kg, i.e. about 250 ml/min for a subject weighting 70 kgs. Applying the equations (3) and (7), the oxygen delivery (DO2) may be calculated, and is about 1000 mL/min. Therefore, a considerable functional reserve exists, since the DO2 is about 4 times greater than the VO2. The VO2 may increase depending on the metabolic needs (basically under physical exercise, but even in pathologic conditions like septic shock). A top level endurance athlete may reach a maximal VO2 of about 5,000 mL/min.

Of course, to meet these increasing oxygen demands, the DO2 must increase as well: it can reach, in an athlete during exercise, the value of 6,000 mL/min (Qc: 30 L/min with an unchanged arterial oxygen content of 20 mL/dL). As a consequence, the O2 ER may increase up to 75%.

FIG. 1 is a diagram showing the relationship between DO2 and VO2 in an athlete during physical exercise. If the athlete (that, for example, is running a marathon) falls into the dark triangular zone (where the DO2 is unable to support the VO2), he is forced to use other metabolic mechanisms in order to develop mechanical energy. As a matter of fact, he will use the anaerobic lactacid metabolism, which develops energy but at the expenses of lactic acid formation, local and systemic acidosis, and finally exercise stops usually within 2 minutes. In other words, the VO2 is physiologically dependent on the DO2.

In the medical field, of course, the situation is different. The DO2 may pathologically decrease in case of: decreased arterial oxygen content due to anemia; decreased arterial oxygen content due to hypoxia; and decreased cardiac output.

However, due to the existence of the above-mentioned physiological reserve, the VO2 may be maintained even for a DO2 decrease down to about 600 mL/min (DO2i 320 mL/min/m$^2$), due to the increased O2 ER.

FIG. 2 is a diagram showing the relationship between DO2 and VO2 in the range observed during medical conditions (i.e. cardiac operation). Below a DO2 of 600 mL/min, the VO2 starts decreasing. The patient meets, exactly as the athlete, a lactic acidosis, with lactates (LAC) production. In other words, he experiences a shock.

The DO2 level below which the VO2 starts decreasing and becomes pathologically dependent on the DO2 is called the critical DO2 ($DO2_{crit.}$). Maintaining the DO2 above this threshold is very important in many pathological conditions, to avoid an acidosis-shock status. The $DO2_{crit.}$ is higher during a septic shock.

Since 1994, in a paper published in Perfusion, Ranucci and coworkers demonstrated that in a series of 300 consecutive patients that underwent myocardial revascularization with CPB, the presence of a severe hemodilution was an independent risk factor for a postoperative acute renal failure (ARF). In particular, the cut-off value was identified at an HCT<25%.

Subsequently, other authors have demonstrated that the lowest HCT during CPB was an independent risk factor for many "adverse outcomes" in cardiac surgery. Stafford-Smith and coworkers, in 1998 (*Anesth Analg*), confirmed the relationship between hemodilution and ARF.

More recently, the lowest hematocrit on CPB has been recognized as an independent risk factor for postoperative low cardiac output and hospital mortality by Fang and coworkers (*Circulation*, 1997), and for an impressive series of postoperative adverse events by Habib and coworkers in 2003 (*J Thorac Cardiovasc Surg*). The relationship between hemodilution and ARF has been subsequently confirmed by Swaminathan and coworkers in 2003 (*Ann Thorac Surg*), Ranucci and coworkers 2004 and 2005 (*Ann Thorac Surg*) and Karkouti and coworkers in 2005 (*J Thorac Cardiovasc Surg*). The critical HCT value below which the ARF risk significantly increases is located between 23% and 26%.

Almost all the authors ascribe this relationship to an insufficient oxygen supply (DO2) to the various organs. The kidney, in particular, due to its physiologic condition of hypoxic perfusion, seems to be at high risk.

Surprisingly, all the studies demonstrating a relationship between HCT and ARF or other organ damages failed to consider that the HCT is only one of the two determinants of the DO2 during CPB: the other is the pump flow (Qp). This would not influence the DO2 if the Qp was a constant, but this is not the case. In all the studies, the pump flow (Qp) varied from a Qpi of 2.0 L/min/m$^2$ to a Qpi of 3.0 L/min/m$^2$, and the variation was dependent on the perfusion pressure. An HCT of 24% results in a DO2i of 230 ml/min/m$^2$ if the Qpi is 2.0 L/min/m$^2$, and of 344 ml/min/m$^2$ if the Qpi is 3.0 L/min/m$^2$.

In a scientific paper in *The Annals of Thoracic Surgery*, not published at the priority dates of the present application, Ranucci and coworkers actually demonstrated that the DO2i, rather than the HCT, is the best predictor of ARF. Moreover, in presence of perioperative blood transfusions, the DO2i remains the only determinant of ARF. The $DO2_{crit}$ identified in this paper is 272 ml/min/m$^2$, very close to the one previously defined as the DO2i below which the VO2 becomes pathologically dependent on the DO2. In other words, maintaining the DO2i above this threshold allows a decrease in the hypoxic organ dysfunction or the elimination of the hypoxic organ dysfunction; in presence of a low HCT, an adequate increase of the Qp may minimize the deleterious effects of hypoxemia. As a consequence, a continuous monitoring of the DO2 is of paramount importance in order to limit the postoperative complications, namely the renal ones.

Measuring a low HCT has poor clinical value, since the only possible (and arguable) countermeasure is a blood transfusion. On the other hand, the DO2 may be modulated by increasing the pump flow.

The level of $DO2_{crit}$, below which the LAC production begins, is identified by the concept of "anaerobic threshold"

(AT). In athletes, it is the level of expressed mechanical power at which the LAC production begins; in a patient, it is the level of $DO2_{crit}$, below which the LAC production begins.

It has been demonstrated that the LAC value during CPB is predictive for postoperative complications. The problem is that the LAC value is not available on-line, and only some devices (blood gas analyzers) provide it. It is however possible to make an "indirect" assessment of the AT. As a matter of fact, under steady conditions, the VO2/VCO2 ratio is a constant, while during anaerobic lactacid metabolism the VCO2 increases more than the VO2. This happens because the lactic acid undergoes the following transformation:

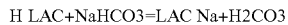

H LAC+NaHCO3=LAC Na+H2CO3 and the H2CO3 is split into H2O and CO2, with a further CO2 production.

FIG. 3 is a diagram showing the relationship between VO2 and VCO2. The relationship between VCO2 and LAC production has been demonstrated in 15 consecutive patients under CPB, in an experimental trial performed by the inventor himself. In FIG. 4 the graphical relationship between VCO2 and LAC production is reported. From this relationship, it appears that a VCOi value of 60 ml/min/m² is a sensitive predictor of lactic acidosis.

Based on the previous experimental information, according to the invention, a monitoring system for cardiac operations with CPB has been developed. This monitoring system includes:

a processor connected to a heart-lung machine;

a pump flow reading device, connected to a pump of the heart-lung machine, to continuously measure the pump flow and to send the pump flow data to the processor;

a hematocrit value reading device, inserted inside the venous or arterial line, to continuously measure the hematocrit value and to send it to the processor;

a data input device, to allow the operator to manually input the data regarding the arterial oxygen saturation (Sat(a)) and the arterial oxygen tension (PaO2);

computing means integrated in the processor, to compute the oxygen delivery (DO2i) value on the basis of the measured pump flow (Qp), the measured hematocrit (HCT), the preset value of arterial oxygen saturation (Sat(a)), and the preset value of arterial oxygen tension (PaO2); and a display connected to the processor, to visualize in real-time the value of DO2i calculated.

Advantageously, the system may be implemented with a CO2 reading device, to continuously detect the exhaled CO2 (eCO2) at the oxygenator gas escape of the heart-lung machine. The data input device allows the operator to insert the gas flow value (Ve), the computing means computes the CO2 production (VCO2i) on the basis of the preset gas flow (Ve) value and the detected exhaled CO2 (eCO2), and the display shows the calculated value of CO2 production (VCO2i).

In one embodiment, the invention provides a monitoring system further comprising: comparing means to compare the above mentioned oxygen delivery (DO2i) value with a threshold value of oxygen delivery ($DO2i_{crit}$); and an alarm which is triggered when the oxygen delivery (DO2i) value falls below the threshold value of oxygen delivery ($DO2i_{crit}$). In one embodiment, the threshold value of oxygen delivery ($DO2i_{crit}$) is preset by the operator at a value of about 270 ml/min/m². In one embodiment, the monitoring system further comprises a temperature detecting device able to continuously measure the body temperature (T) of the patient and to send the temperature values to the processor, to be subsequently displayed by the display. The monitoring system can further comprise an oxygen delivery threshold computing means, receiving as input the temperature (T) value of the patient as detected.

In one embodiment of the monitoring system, the processor includes a hemoglobin value computing means able to calculate the hemoglobin (Hb) value from the detected hematocrit (HCT) value, and to send it to the oxygen delivery computing means, to be subsequently displayed in the display. In another embodiment of the monitoring system, the processor includes a computing means able to calculate the indexed pump flow (Qpi) from the pump flow (Qp) and the value of body surface area (BSA) of the patient. In an embodiment of the monitoring system, the data input device can allow the operator to manually input data regarding the weight and height of the patient so that the computing means is able to compute the body surface area (BSA) of the patient. In one embodiment, the pump flow detecting device includes a Doppler reading cell.

The invention provides a monitoring system for cardiac operations with cardiopulmonary bypass comprising: a processor operatively connected to a heart-lung machine; a CO2 detecting device placed at the oxygenator of the heart-lung machine to continuously detect the exhaled CO2 (eCO2) value and send it to the processor; a data input device allowing the operator to manually input data regarding the gas flow (Ve) of the heart-lung machine; computing means able to calculate the CO2 production (VCO2i) from the preset gas flow (Ve) and the exhaled CO2 (eCO2) detected; and a display connected to the processor to display in real-time the above CO2 production (VCO2i) as calculated. In one embodiment, the monitoring system further comprises comparison means to compare the above CO2 production (VCO2i) calculated value with a CO2 production threshold value ($VCO2i_{crit}$); and an alarm that is triggered whenever the CO2 production (VCO2i) value exceeds the CO2 production threshold value ($VCO2i_{crit}$).

The invention provides a method of monitoring a patient's parameters during a cardiac operation with cardiopulmonary bypass and a heart-lung machine, the method comprising: continuously detecting the pump flow (Qp) from a pump of the heart-lung machine; continuously detecting the hematocrit (HCT) value from the arterial or venous line of the heart-lung machine; setting an arterial oxygen saturation (Sat (a)) value derived from the arterial blood of the patient; setting an arterial oxygen tension (PaO2) value derived from the arterial blood of the patient; computing the oxygen delivery (DO2i) of the patient from the detected and set values; and displaying the oxygen delivery (DO2i) value as calculated. In one embodiment the method further comprises: setting an oxygen delivery threshold ($DO2i_{crit}$) value; comparing the calculated oxygen delivery (DO2i) value with the oxygen delivery threshold ($DO2i_{crit}$) value; and triggering a warning signal whenever the calculated oxygen delivery (DO2i) value falls below the set oxygen delivery threshold ($DO2i_{crit}$) value. In one embodiment, the warning signal is not triggered when the calculated oxygen delivery (DO2i) value falls below the set oxygen delivery threshold ($DO2i_{crit}$) value for a period of time shorter than a preset time period. In one embodiment, the method further comprises the continuous detection and display of the patient's temperature (T). In one embodiment, the method comprises calculating the oxygen delivery threshold ($DO2i_{crit}$) value from the detected body temperature (T).

The invention provides a method of monitoring a patient's parameters during a cardiac operation with cardiopulmonary bypass and a heart-lung machine, the method comprising: continuously detecting the exhaled carbon dioxide (eCO2) from the oxygenator of the heart-lung machine; setting a gas flow (Ve) value of the heart-lung machine; computing the carbon dioxide production (VCO2i) of the patient from the detected values of exhaled carbon dioxide (eCO2) and set values of gas flow (Ve); and displaying the calculated carbon dioxide production (VCO2i) value. In one embodiment, the method further comprises: setting a carbon dioxide production threshold ($VCO2i_{crit}$) value; comparing the calculated carbon dioxide production (VCO2i) value with the set carbon dioxide production threshold ($VCO2i_{crit}$) value; and triggering a warning signal whenever the calculated carbon dioxide production (VCO2i) value exceeds the set carbon dioxide production threshold ($VCO2i_{crit}$) value.

The invention provides a monitoring system for cardiac surgical operations comprising: a processor connected to a heart-lung machine; pump flow reading device connected to a pump of the heart-lung machine for measuring the value of the pump flow (Qp) and sending it to the processor; blood hematocrit (HCT) value reading device connected to the heart-lung machine circuit for measuring the HCT value and sending it to the processor; CO2 detecting device to detect the exhaled CO2 (eCO2) at the oxygenator gas escape, data input device to manually input data relative to the arterial oxygen saturation (Sat(a)), arterial oxygen tension (PaO2), and gas flow (Ve); and computing means to compute the oxygen delivery value (DO2i) and the CO2 production value (VCO2i) on the basis of the detected and set values, and a display connected to the processor, to show the calculated values of (DO2i) and (VCO2i).

Further characteristics of the invention will be clarified by the following detailed description, referring to a non-limiting embodiment thereof illustrated in the attached drawings.

FIG. 1 is a graph illustrating the relationship between VO2 and DO2 in an athlete under physical exercise.

FIG. 2 is a graph illustrating the relationship between VO2 and DO2 in a patient under cardiac operation.

FIG. 3 is a graph illustrating the relationship between VCO2 and VO2.

FIG. 4 is a graph illustrating the relationship between LAC and VCO2i.

In the following description, and with reference to FIGS. 5, 6, 7, and 8, the monitoring system for cardiac operations with cardiopulmonary bypass is described, according to the invention.

Figure 5:
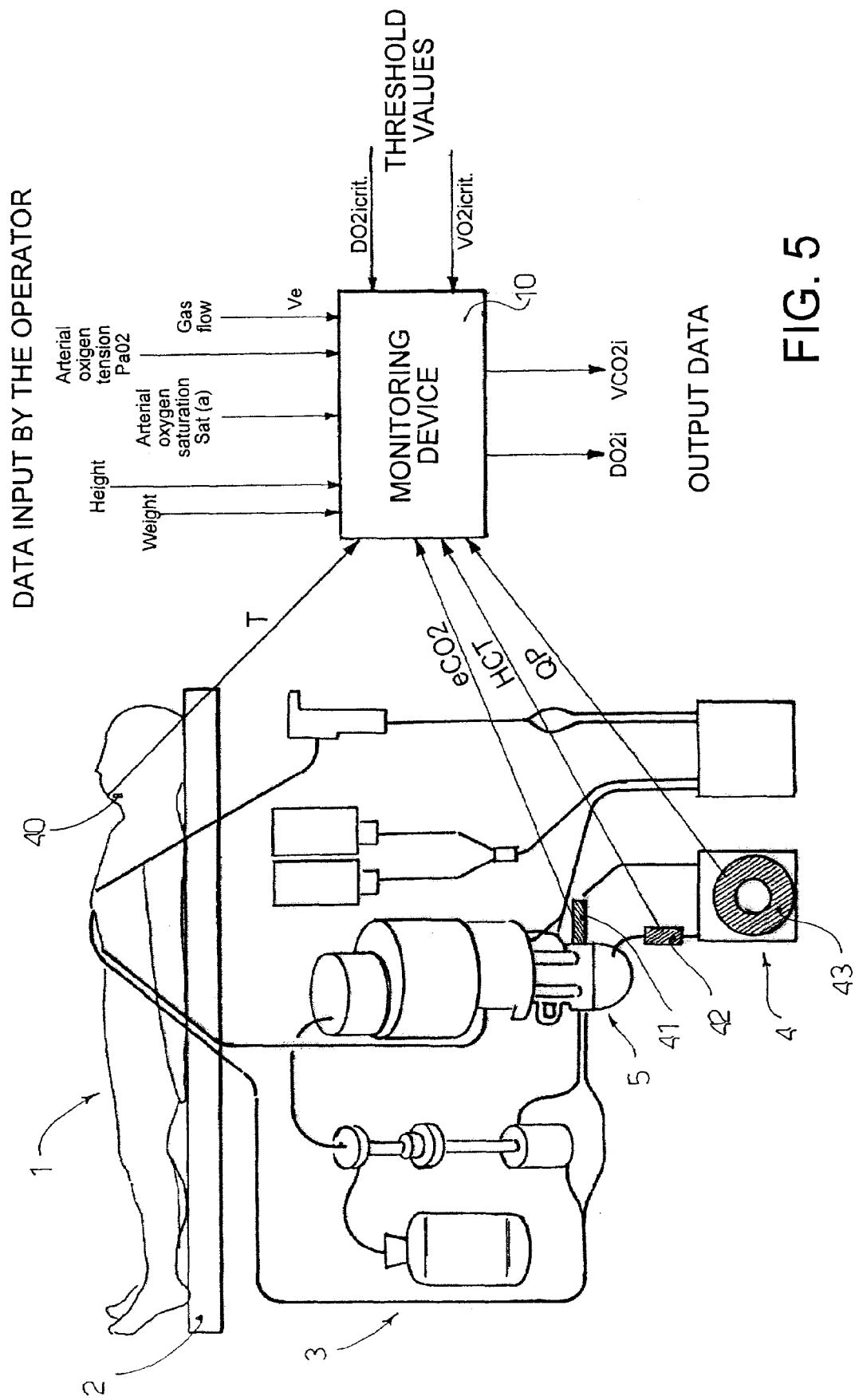
FIG. 5 is a schematic view of a heart-lung machine connected to the patient and a block diagram of a monitoring system according to the invention.

FIG. 5 shows a patient 1 laying on a surgical table 2. A heart-lung machine, comprehensively identified by the number 3, is connected to the patient 1. As already known in the art, a heart-lung machine 3 comprises a venous extracorporeal circuit, collecting blood from the venous system of the patient. A roller or centrifugal mechanical pump 4 pumps the venous blood from a venous extracorporeal circuit towards an oxygenator 5, whose role is removing CO2 from the venous blood and supplying oxygen (O2). The blood oxygenated by the oxygenator 5, is sent, again by the same roller or centrifugal pump 4, to an arterial extracorporeal circuit connected to the arterial system of the patient, therefore creating a total bypass of the heart and lungs of the patient.

The monitoring system, according to the invention, comprehensively identified by the reference number 10, is operatively connected to the heart-lung machine 3. The monitoring system 10 comprises a processor able to perform calculations, as subsequently explained, and a monitor screen or display 11 that works as an interface with the operator.

Manual Data Input from the Operator

Using the knob 50 (FIGS. 7 and 8), placed in the front part of the monitoring system 10, the operator may input data that will be stored by the processor memory of the monitoring system 10. Data manually inserted by the operator are:

(1) Height and weight of the patient.

(2) The arterial oxygen saturation (Sat(a)). This value, during CPB procedures, is usually 100%. However, in case of extraordinary events like an oxygenator malfunction, the value of (Sat(a)) may decrease. In this case, the operator may manually change this value using the knob 50.

(3) The arterial oxygen tension (PaO2) value. This PaO2 value is measured by the perfusionist on the arterial blood of the patient with blood gas analysis, using an adequate and specific device.

(4) The gas flow value (Ve). This Ve value is established by the perfusionist operating the heart-lung machine 3. Generally, the Ve is regulated with a flow-meter, in a range between 1 and 5 L/min, according to the patient's parameters. This Ve value rarely changes during a CPB procedure, and therefore can be manually inserted by the operator. However, as an alternative, the monitoring system 10 may include an electronic flow-meter connected to the heart-lung machine 3, to continuously detect the Ve value.

Heart-Lung Machine Interfaced Data

The monitoring device 10 is equipped with some electrical connections to the heart-lung machine 3, as to continuously receive data collected by adequate sensors placed in specific positions of the heart-lung machine. These continuously collected data are:

(1) Patient's body temperature (T). This temperature T is continuously measured by a temperature probe inserted inside the esophagus or the rectum of the patient. The temperature probe 40 sends an electronic signal of the temperature to a monitor of the heart-lung machine visualizing, in real-time, the temperature value. In this case, it is sufficient to interface with an electrical connection the monitor of the heart-lung machine 3 with the monitoring device 10, for a continuous input of the temperature value T.

(2) Exhaled carbon dioxide (eCO2). This eCO2 value is continuously measured through a CO2 detector 41 placed at the gas escape of the oxygenator 5 to detect the sidestream CO2 exhaled from the oxygenator 5. The CO2 detector 41 can be any kind of CO2 detector among the various commercially available and re-usable capnographs.

(3) Hematocrit (HCT). The HCT value is continuously measured through a hematocrit reading cell 42 placed inside the arterial or venous circuit of the heart-lung machine 3. For instance, in FIG. 5, the hematocrit reading cell 42 is placed inside the arterial line between the pump 4 and the oxygenator 5. The hematocrit reading cell 42 is commercially available and disposable.

(4) Pump flow (Qp). The Qp value is continuously measured through the Doppler reading cell 43, placed on the arterial line of the heart-lung machine 3. This kind of Doppler reading cell 43 measures the blood flow on the basis of the Doppler principle (red cells velocity).

If the pump 4 of the extracorporeal circuit is a centrifugal pump, it is already equipped with the Doppler reading cell 43. Conversely, if the pump 4 is a roller pump, the Doppler reading cell 43 may be added. In the alternative, the Doppler reading cell 43 may be omitted, since the roller pump head is provided with a flow measuring system. In this case, the data regarding the pump flow Qp is directly sent to the monitoring device 10.

With specific reference to FIG. 6, the operation of the monitoring system 10 is described below. The processor of the monitoring system 10 includes a first computing program 12 that, based on the weight and height of the patient as input by the operator calculates, according to pre-defined tables, the body surface area (BSA) of the patient.

The BSA value is sent to a second computing program 13 that receives the input value of the pump flow Qp as detected by the pump 4 of the heart-lung machine 3. The second computing program 13 calculates the indexed pump flow Qpi, according to the relationship QpI=Qp/BSA.

A third computing program 14 receives the input value HCT as detected by the hematocrit reading cell 43 placed inside the venous or arterial line of the heart-lung machine. The third computing program 14, based on the equation (6), calculates the hemoglobin value Hb. The Hb value is sent to the display 11 and displayed in a window 51 of the display 11 (FIG. 7).

The pump flow indexed Qpi computed by the second computing program 13 and the hemoglobin value Hb computed by the third computing program 14 are sent to a fourth computing program 15 that receives as input values the values of arterial oxygen saturation (Sat(a)) and arterial oxygen tension (PaO2) manually entered by the operator. The fourth computing program 15, according to the equation (4), calculates the indexed oxygen delivery value (DO2i).

Figure 7:
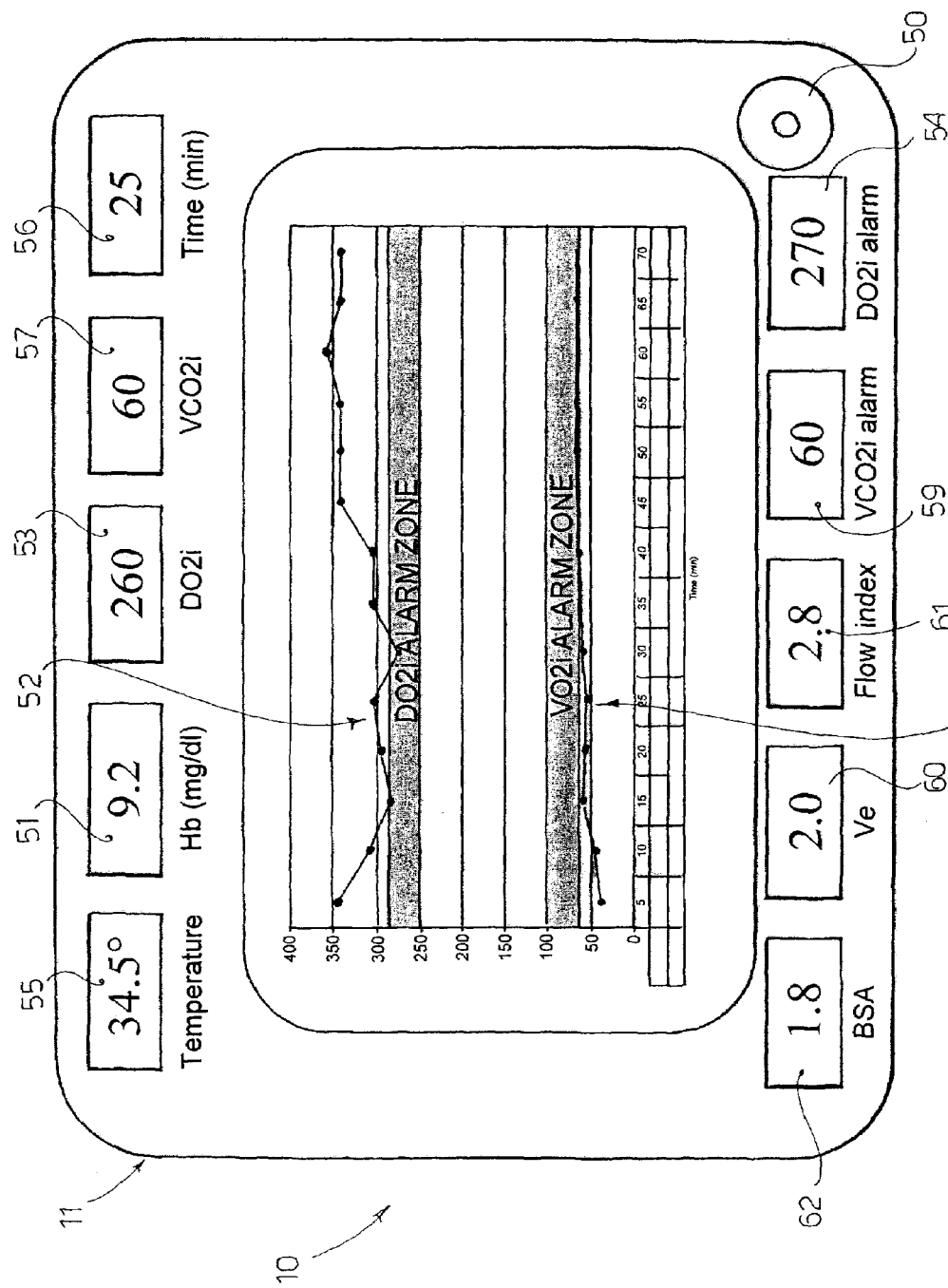
FIG. 7 is a front view of a monitoring device according to the invention, showing a screen view of the display.

As shown in FIG. 7, the DO2i value is visualized in real time in a window 53 of the display 11 and as a graphical pattern 52 (as a function of time). The display 11 is provided with a chronometer window 56 showing the time passed from the beginning of the CPB.

Figure 6:
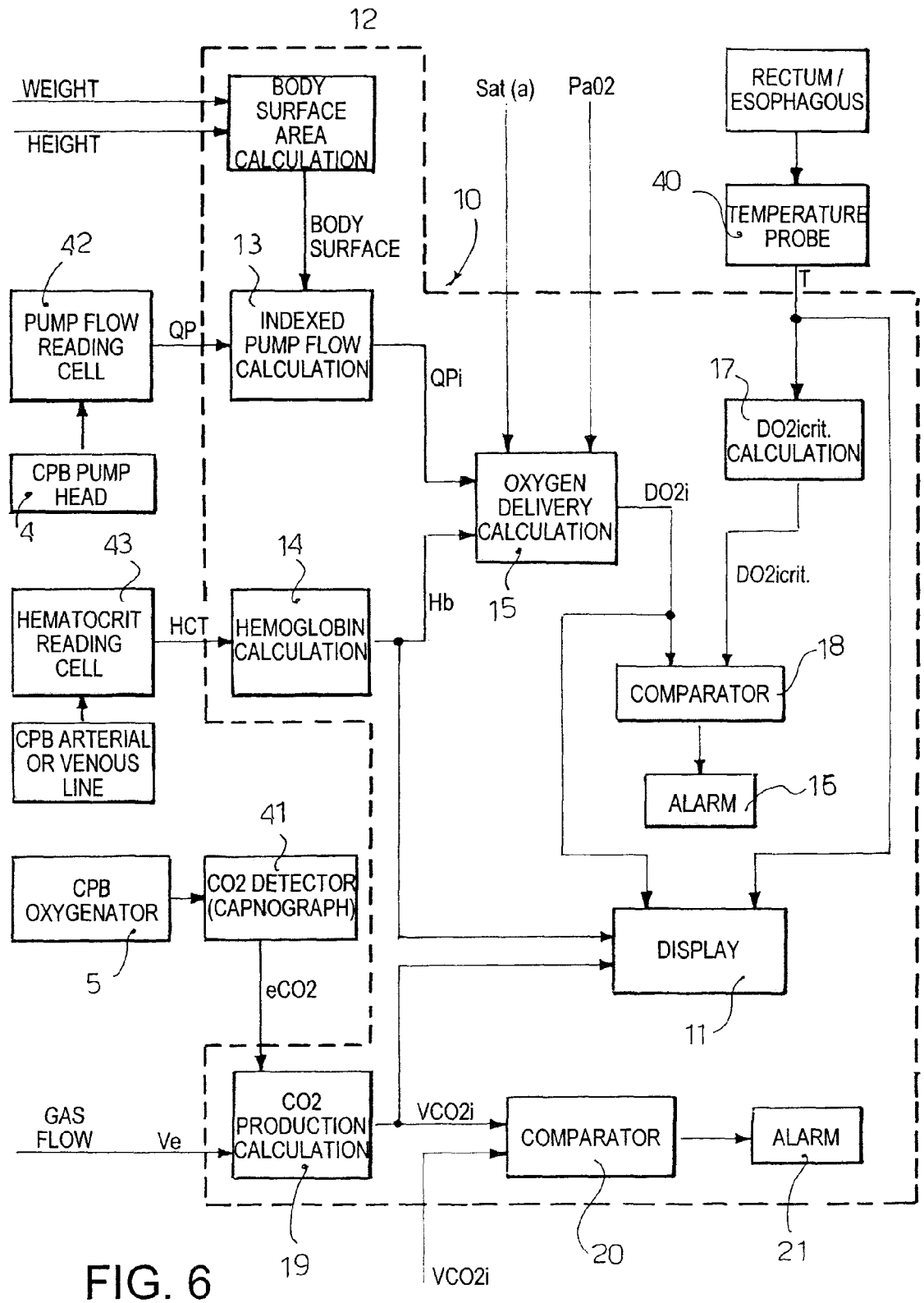
FIG. 6 is a block diagram illustrating in a more detailed way a monitoring system according to the invention.

As shown in FIG. 6, the DO2i value is sent to a comparator 18 which compares it to a threshold value of $DO2i_{crit}$ that is displayed in a window 54 (FIG. 7) of the display 11. This threshold value is set at 270 ml/min/m² at a temperature between 34° C. and 37° C., and decreases as a function of temperature, in a linear fashion.

Therefore the threshold value of $DO2i_{crit}$ be preset by the operator or may be calculated by a computing program 17 depending on the temperature value T determined by the temperature probe 40. The temperature T value determined by the probe 40 is sent to the display 11 to be displayed in a window 55.

When the DO2i value falls below the $DO2i_{crit}$, the comparing device 16 sends a control signal to an alarm 16 that is triggered, alerting the operator of a potentially dangerous condition.

The alarm 16 is not triggered by brief decreases of the pump flow Qp (often needed during CPB). Therefore, the alarm 16 could be set to be activated after 5 minutes of consecutive detection of a DO2i below the $DO2i_{crit}$. However, a recording of all the periods of low flow can be made, to analyze and avoid the possibility that many short periods of low flow may create an additional effect. It is reasonable to consider no more than 20 minutes (as a total) of DO2i below the $DO2i_{crit}$ during a normal CPB lasting about 90 minutes. The monitoring device 10 is equipped with a computing program 19, which receives as input values the exhaled carbon dioxide eCO2 as detected by the CO2 sensor 41 and the gas flow Ve set by the operator. According to these input data, the computing program 19 calculates the indexed carbon dioxide production VCO2i applying the equation (9).

The VCO2i value as calculated by the computing program 19 is sent to the display 11 and displayed in real time in a window 57 (FIG. 7) in its graphical relationship 58 as a function of time.

The VCO2i value is sent to a second comparator 20 which compares it with an anaerobic threshold value $VCO2i_{crit}$ set by the operator; by default the $VCO2i_{crit}$ is preset at 60 ml/min/m². As shown in FIG. 7, the display 11 is provided with a window 59 showing the value of anaerobic threshold $VCO2i_{crit}$ set by the operator.

Back to FIG. 6, when the VCO2i exceeds the $VCO2i_{crit}$ an alarm signal is sent to a second alarm 21, which, when triggered, alerts the operator of a warning condition. Moreover, as shown in FIG. 7, the display 11 is provided with: a window 60 where the gas flow value Ve set by the operator is displayed; a window 61 where the indexed pump flow value Qpi arriving from the computing program 13 is displayed; and a window 62 where the body surface area of the patient is displayed as calculated by the computing program 12.

Figure 8:
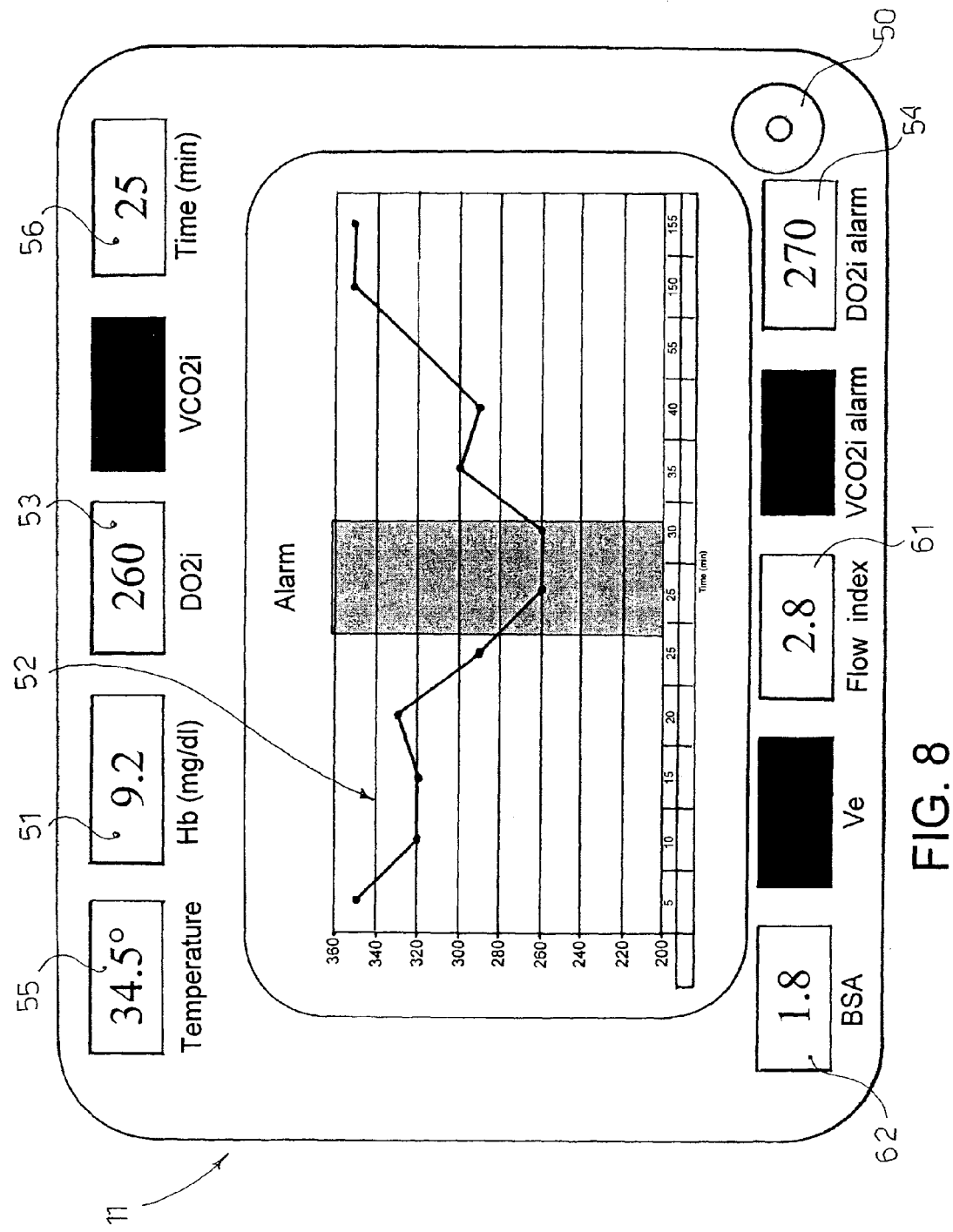
FIG. 8 is a view of a monitoring device according to the invention similar to FIG. 7, in a minimal configuration.

The monitoring system 10 can be equipped with a data recording system and a printer interface, and/or a digital data recording system. The display 11 could include two configurations: a complete configuration, as the one shown in FIG. 7, and a reduced configuration, only considering the DO2 parameter, as shown in FIG. 8.

The above description and accompanying drawings are provided for the purpose of describing embodiments of the invention and are not intended to limit the scope of the invention in any way. It will be apparent to those skilled in the art that various modifications and variations can be made in the systems and methods for cardiac operations without departing from the spirit or scope of the invention. Thus, it is intended that the present invention cover the modifications and variations of this invention provided they come within the scope of the appended claims and their equivalents.

REFERENCES

1. Ranucci M, Pavesi M, Mazza E, et al. Risk factors for renal dysfunction after coronary surgery: the role of cardiopulmonary bypass technique. Perfusion 1994; 9: 319-26.
2. Stafford-Smith M, Conlon P J, White W D, et al. Low hematocrit but not perfusion pressure during CPB is predictive for renal failure following CABG surgery [Abstract]. Anesth Analg 1998; 86: SCA 11-124.
3. Fang W C, Helm R E, Krieger K H, et al. Impact of minimum hematocrit during cardiopulmonary bypass on mortality in patients undergoing coronary artery surgery. Circulation 1997; 96 (suppl II): 194-9.
4. Habib R H, Zacharias A, Schwann T A, Riordan C J, Durham S J, Shah A. Adverse effects of low hematocrit during cardiopulmonary bypass in the adult: should current practice be changed? J Thorac Cardiovasc Surg 2003; 125: 1438-50.
5. Swaminathan M, Phillips-Bute B G, Conlon P J, Smith P K, Newman M F, Stafford-Smith M. The association of lowest hematocrit during cardiopulmonary bypass with acute renal injury after coronary artery bypass surgery. Ann Thorac Surg 2003; 76: 784-92.
6. Karkouti K, Beattie W S, Wijeysundera D N, et al. Hemodilution during cardiopulmonary bypass is an independent risk factor for acute renal failure in adult cardiac surgery. J Thorac Cardiovasc Surg 2005; 129: 391-400.
7. Ranucci M, Romitti F, Isgró G, et al. Oxygen delivery during cardiopulmonary bypass and acute renal failure following coronary operations. Ann Thorac Surg 2005; in press.

8. Ranucci M, Menicanti L, Frigiola A. Acute renal injury and lowest hematocrit during cardiopulmonary bypass: not only a matter of cellular hypoxemia. Ann Thorac Surg 2004; 78: 1880-1.
9. Demers P, Elkouri S, Martineau R, et al. Outcome with high blood lactate levels during cardiopulmonary bypass in adult cardiac surgery. Ann Thorac Surg 2000; 70: 2082-6.

What is claimed is:

1. A method of monitoring a patient's parameters during a cardiac operation with cardiopulmonary bypass and a heart-lung machine including a processor, the heart-lung machine operably connected to an oxygenator configured for oxygenating blood, the method comprising:
   continuously detecting carbon dioxide exiting (eCO2) the oxygenator;
   setting a gas flow (Ve) value of the heart-lung machine via an input device;
   using the processor to calculate a computing the carbon dioxide production (VCO2i) value of the patient from the eCO2 values and set values of gas flow (Ve); and
   displaying the calculated carbon dioxide production (VCO2i) value on a display.

2. A method according to claim 1, further comprising:
   setting a carbon dioxide production threshold ($VCO2i_{crit}$) value;
   comparing the calculated carbon dioxide production (VCO2i) value with the set carbon dioxide production threshold ($VCO2i_{crit}$) value; and
   triggering a warning signal whenever the calculated carbon dioxide production (VCO2i) value exceeds the set carbon dioxide production threshold ($VCO2i_{crit}$) value.

3. A method of monitoring a patient's parameter during a cardiac operation with cardiopulmonary bypass and a heart-lung machine including a processor, the method comprising:
   detecting carbon dioxide exiting (eCO2) from an oxygenator of the heart-lung machine;
   setting a gas flow (Ve) value of the heart-lung machine via an input device;
   using the processor to calculate a carbon dioxide production (VCO2i) value of the patient from the eCO2 values and set values of gas flow (Ve); and
   displaying the calculated carbon dioxide production (VCO2i) value on a display.

4. A method according to claim 3, further comprising:
   setting a carbon dioxide production threshold ($VCO2i_{crit}$) value;
   comparing the calculated carbon dioxide production (VCO2i) value with the set carbon dioxide production threshold ($VCO2i_{crit}$) value; and
   triggering a warning signal whenever the calculated carbon dioxide production (VCO2i) value exceeds the set carbon dioxide production threshold value ($VCO2i_{crit}$) value.

5. A method of monitoring a patient's parameters during a cardiac operation with cardiopulmonary bypass and a heart-lung machine including a processor, the heart-lung machine operably connected to an oxygenator configured for oxygenating blood, the method comprising:
   using a CO2 detector to detect CO2 exiting the oxygenator and provide an exiting carbon dioxide (eCO2) value;
   setting a gas flow (Ve) value of the heart-lung machine via an input device; using the processor to calculate a carbon dioxide production (VCO2i) value of the patient from the eCO2 values and set values of gas flow (Ve);
   displaying the calculated carbon dioxide production (VCO2i) value on a display;
   setting a carbon dioxide production threshold ($VCO2i_{crit}$) value;
   comparing the calculated carbon dioxide production (VCO2i) value with the set carbon dioxide production threshold ($VCO2i_{crit}$) value; and
   triggering a warning signal whenever the calculated carbon dioxide production (VCO2i) value exceeds the set carbon dioxide production threshold ($VCO2i_{crit}$) value.

* * * * *

UNITED STATES PATENT AND TRADEMARK OFFICE
CERTIFICATE OF CORRECTION

PATENT NO.       : 7,931,601 B2                                          Page 1 of 1
APPLICATION NO.  : 12/250221
DATED            : April 26, 2011
INVENTOR(S)      : Marco Ranucci It is certified that error appears in the above-identified patent and that said Letters Patent is hereby corrected as shown below:

Column 11, line 18, delete "computing the"

Column 11, line 20, replace "eCO2" with --(eCO2)--

Column 12, line 2, replace "eCO2" with --(eCO2)--

Column 12, line 26, replace "eCO2" with --(eCO2)--

Signed and Sealed this

Seventh Day of February, 2012

David J. Kappos
*Director of the United States Patent and Trademark Office*